(12) United States Patent
Theofilos et al.

(10) Patent No.: US 9,827,114 B2
(45) Date of Patent: Nov. 28, 2017

(54) LATERAL DISTRACTOR

(71) Applicant: K2M, Inc., Leesburg, VA (US)

(72) Inventors: Charles Theofilos, Palm Beach Gardens, FL (US); Todd Wallenstein, Ashburn, VA (US); Adam Wassinger, Reston, VA (US); Scott Jones, McMurray, PA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 14/994,476

(22) Filed: Jan. 13, 2016

(65) Prior Publication Data

US 2016/0120663 A1    May 5, 2016

Related U.S. Application Data

(63) Continuation of application No. 14/058,626, filed on Oct. 21, 2013, now Pat. No. 9,241,700.

(60) Provisional application No. 61/716,502, filed on Oct. 20, 2012.

(51) Int. Cl.
| | |
|---|---|
| *A61F 2/46* | (2006.01) |
| *A61B 17/02* | (2006.01) |
| *A61F 2/44* | (2006.01) |
| *A61B 17/08* | (2006.01) |
| *A61F 2/30* | (2006.01) |

(52) U.S. Cl.
CPC .......... *A61F 2/4611* (2013.01); *A61B 17/025* (2013.01); *A61B 17/0206* (2013.01); *A61B 17/083* (2013.01); *A61F 2/4465* (2013.01); *A61F 2002/30481* (2013.01); *A61F 2002/30556* (2013.01); *A61F 2002/30579* (2013.01); *A61F 2002/30774* (2013.01); *A61F 2002/30827* (2013.01); *A61F 2002/30836* (2013.01); *A61F 2002/30841* (2013.01); *A61F 2002/4475* (2013.01); *A61F 2002/4622* (2013.01); *A61F 2002/4623* (2013.01); *A61F 2002/4627* (2013.01); *A61F 2002/4628* (2013.01)

(58) Field of Classification Search
CPC ............................ A61F 2/4611; A61B 17/025
See application file for complete search history.

(56) References Cited

U.S. PATENT DOCUMENTS

| | | | |
|---|---|---|---|
| 6,562,074 B2 * | 5/2003 | Gerbec | A61F 2/4455 623/17.15 |
| 6,863,673 B2 | 3/2005 | Gerbec et al. | |

(Continued)

*Primary Examiner* — David Bates
*Assistant Examiner* — Olivia C Chang
(74) *Attorney, Agent, or Firm* — Carter, DeLuca, Farrell & Schmidt, LLP

(57) ABSTRACT

A distraction device includes a cage distractor, two distractor blades, an inserter positioner, and a clip inserter. The cage distractor is selectively securable to the two distractor blades and includes two distractor housings moveable relative to one another. The inserter positioner is selectively securable to the two distractor blades and include a center member that is centered between the distractor blades when the inserter positioner is secured to the two distractor blades. The clip inserter is configured to secure a clip to a distal end thereof and is slidable through the center member to secure the clip to a cage distracted by the movement of the two distractor housings away from one another. The clip maintaining the distraction of the cage.

4 Claims, 17 Drawing Sheets

(56) References Cited

U.S. PATENT DOCUMENTS

| | | | |
|---|---|---|---|
| 7,118,580 B1* | 10/2006 | Beyersdorff | A61F 2/4611 |
| | | | 606/99 |
| 8,114,088 B2 | 2/2012 | Miller | |
| 8,163,020 B2 | 4/2012 | Le Huec | |
| 8,182,423 B2 | 5/2012 | Miles et al. | |
| 8,202,299 B2 | 6/2012 | Wang et al. | |
| 8,241,294 B2 | 8/2012 | Sommerich et al. | |
| 8,268,004 B2 | 9/2012 | Castleman et al. | |
| 8,273,126 B2 | 9/2012 | Lindner | |
| 8,512,535 B2 | 8/2013 | Coster et al. | |
| 2003/0074064 A1* | 4/2003 | Gerbec | A61F 2/4455 |
| | | | 623/16.11 |
| 2005/0075643 A1* | 4/2005 | Schwab | A61B 17/0206 |
| | | | 606/90 |
| 2005/0245928 A1* | 11/2005 | Colleran | A61B 17/708 |
| | | | 606/90 |
| 2006/0058807 A1* | 3/2006 | Landry | A61F 2/447 |
| | | | 606/90 |
| 2006/0247649 A1* | 11/2006 | Rezach | A61B 17/7077 |
| | | | 606/90 |
| 2008/0077155 A1* | 3/2008 | Diederich | A61B 17/708 |
| | | | 606/105 |
| 2008/0077156 A1 | 3/2008 | Emstad | |
| 2008/0114367 A1 | 5/2008 | Meyer | |
| 2008/0177275 A1* | 7/2008 | Wing | A61F 2/4611 |
| | | | 606/99 |
| 2008/0281424 A1* | 11/2008 | Parry | A61F 2/4455 |
| | | | 623/17.16 |
| 2009/0062918 A1 | 3/2009 | Wang et al. | |
| 2009/0234362 A1 | 9/2009 | Blain et al. | |
| 2011/0184522 A1* | 7/2011 | Melkent | A61F 2/4611 |
| | | | 623/17.16 |
| 2011/0251692 A1* | 10/2011 | McLaughlin | A61F 2/44 |
| | | | 623/17.16 |
| 2013/0006359 A1* | 1/2013 | Fedorov | A61F 2/4465 |
| | | | 623/17.16 |
| 2013/0110113 A1* | 5/2013 | Glazer | A61B 17/7077 |
| | | | 606/90 |

* cited by examiner

LATERAL DISTRACTOR

CROSS-REFERENCE TO RELATED APPLICATIONS

This application is a divisional of U.S. patent application Ser. No. 14/058,626, filed Oct. 21, 2013, which claims priority to, and the benefit of, U.S. Provisional Application Ser. No. 61/716,502, filed Oct. 20, 2012. The entire disclosures of each of the above applications are hereby incorporated by reference.

BACKGROUND

1. Technical Field

The present disclosure relates to spinal surgery and, more specifically, to devices and methods for laterally distracting a corpectomy cage.

2. Discussion of Related Art

Disease, the effects of aging, or physical trauma resulting in damage to the spine has been treated in many instances by fixation or stabilization of the affected vertebra. A wide variety of spinal fixation apparatuses have been employed in surgical procedures for correcting spinal injuries and the effects of spinal diseases.

After a partial or complete discectomy, the normally occupied space between adjacent vertebral bodies is subject to collapse and/or misalignment due to the absence of all or a part of the intervertebral disc. In such situations, the physician may insert one or more prosthetic spacers between the affected vertebrae to maintain normal disc spacing and/or the normal amount of lordosis in the affected region.

Typically, a prosthetic implant is inserted between the adjacent vertebrae and may include pathways that permit bone growth between the adjacent vertebrae until they are fused together. As is typical, the intervertebral spaces are accessed either anteriorly or posteriorly. It would be desirable to access the intervertebral spaces via a lateral approach.

SUMMARY

In an aspect of the present disclosure, a surgical device includes a cage distractor, a first distractor blade, a second distractor blade, an inserter positioner, and a clip inserter. The cage distractor includes first and second distractor housings moveable relative to one another. The first and second distractor blades each include a proximal end portion and a distal end portion. The first and second distractor blades are configured to cooperate with the movement of the first and second distractor housings. The distal end portion of each distractor blade is configured to engage a cage to adjust a height of the cage as the distractor housings move relative to one another. The inserter positioner includes first and second attachment members and a center member. The first attachment member is selectively securable to the proximal end portion of the first distractor blade and the second attachment member is selectively securable to the proximal end portion of the second distractor blade. The center member includes a bore centered between the first and second distractor blades when the first and second attachment members are secured to the first and second distractor blades respectively. The clip inserter includes a cannulated body, a distal end portion, and an inserter shaft. The inserter shaft is insertable through the cannulated body and is configured to secure a clip to the distal end portion of the clip inserter. The clip inserter is slidable through the bore of the center member and configured to engage the clip with the cage.

In aspects of the present disclosure, the proximal end portion of each of the first and second distractor blades may include a protrusion extending from the proximal end portion of the first and second distractor blades. The protrusion may include an upper detent and each attachment member of the clip positioner may include a button. The button of each of the attachment members is selectively engagable with the upper detent of the protrusion to secure a respective one of the first and second distractor blades to a respective one of the first and second attachment members. The proximal end portion of the first distractor blade may be selectively securable to the first distractor housing and the proximal end portion of the second distractor blade may be selectively securable to the second distractor housing. The protrusion may include a lower detent and each distractor housing may include a button, which is selectively engagable with the lower detent of the protrusion to secure a respective one of the first and second distractor blades to a respective one of the first and second distractor housings.

In aspects of the present disclosure, the cage distractor includes a center shaft disposed within a channel defined through the first and second distractor housings. Rotation of the center shaft may move the first and second distractor housings relative to one another. At least one of the first and second distractor housings may include a centering bushing with a threaded section. The threaded section of the centering bushing is selectively engagable with a threaded portion of the center shaft. When the threaded portion of the center shaft is engaged with the threaded section of the centering bushing, rotation of the threaded portion of the center shaft moves the centering bushing to move the first and second distractor housings relative to one another. In embodiments, movement of the distractor housings in opposing directions is equal relative to one another based on the configuration of at least one center bushing that is operatively associated with one of the distractor housings. In some embodiments, movement of the distractor housings in opposing directions is asymmetric relative to one another based on the configuration of at least one center bushing that is operatively associated with one of the distractor housings.

In aspects of the present disclosure, the first attachment member is selectively securable to the first distractor housing and the second attachment member is selectively securable to the second distractor housing. In embodiments, one of the first and second distractor blades defines a passage from the proximal end portion to the distal end portion and the surgical device further includes at least one blade shaft that is insertable through the passage. The blade shaft is configured to engage the cage to couple the cage to the distal end portion of the respective first and second distractor blades. In some embodiments, the center member of the inserter positioner includes a keyway extending from the bore and the clip inserter includes a key extending from the cannulated body. The key is received within the keyway when the clip inserter is slid through the ore to align the distal end portion of the clip inserter with the cage.

In aspects of the present disclosure, a method of distracting a cage includes securing a proximal end portion of a first distractor blade in a first distractor housing of a cage distractor and securing a proximal end portion of a second distractor blade in a second distractor housing of the cage distractor, sliding a distal end portion of the first distractor blade and a distal end portion of the second distractor blade onto a cage, and rotating a center shaft of the cage distractor to move the first distractor housing away from the second distractor housing. When the first distractor housing moves away from the second distractor housing the distal end portion of the first distractor blade moves away from the distal end portion of the section distractor blade to distract the cage. The center shaft is disposed along an axis parallel to the movement of the first distractor housing away from the second distractor housing. The method may include securing one of the first and second distractor blades to the cage with a blade shaft inserted through a passage of the distractor blade and threaded a threaded end of the blade shaft into a threaded hole in the cage.

In aspects of the present disclosure, the method includes securing a clip positioner to the proximal end portion of the first distractor blade and the proximal end portion of the second distractor blade, securing a clip to a distal end portion of a clip inserter, and sliding the clip inserter through a bore of a center member of the clip positioner to center the clip between the distal end portions of the first and second distractor blades. Securing the clip to the distal end portion of the clip inserter may include threading a threaded end of an inserter shaft passed through a lumen of a cannulated body of the clip inserter into a threaded hole in the clip. The bore of the center member may be threaded and the clip inserter may include a handle having a threaded handle end. The handle may be rotatable about the cannulated body portion of the clip inserter such that securing the clip onto the cage includes threading the threaded handle end into the bore.

In aspects of the present disclosure, a kit includes a clip and a distraction device. The distraction device may be any of the distraction devices described herein. The kit may include a plurality of clips. Each of the plurality of clips having a different width to maintain a different height of distraction of the cage. The kit may also include a plurality of pairs of first and second distraction blades where each of the pairs of first and second distraction blades define different lengths between the proximal and distal end portions thereof.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
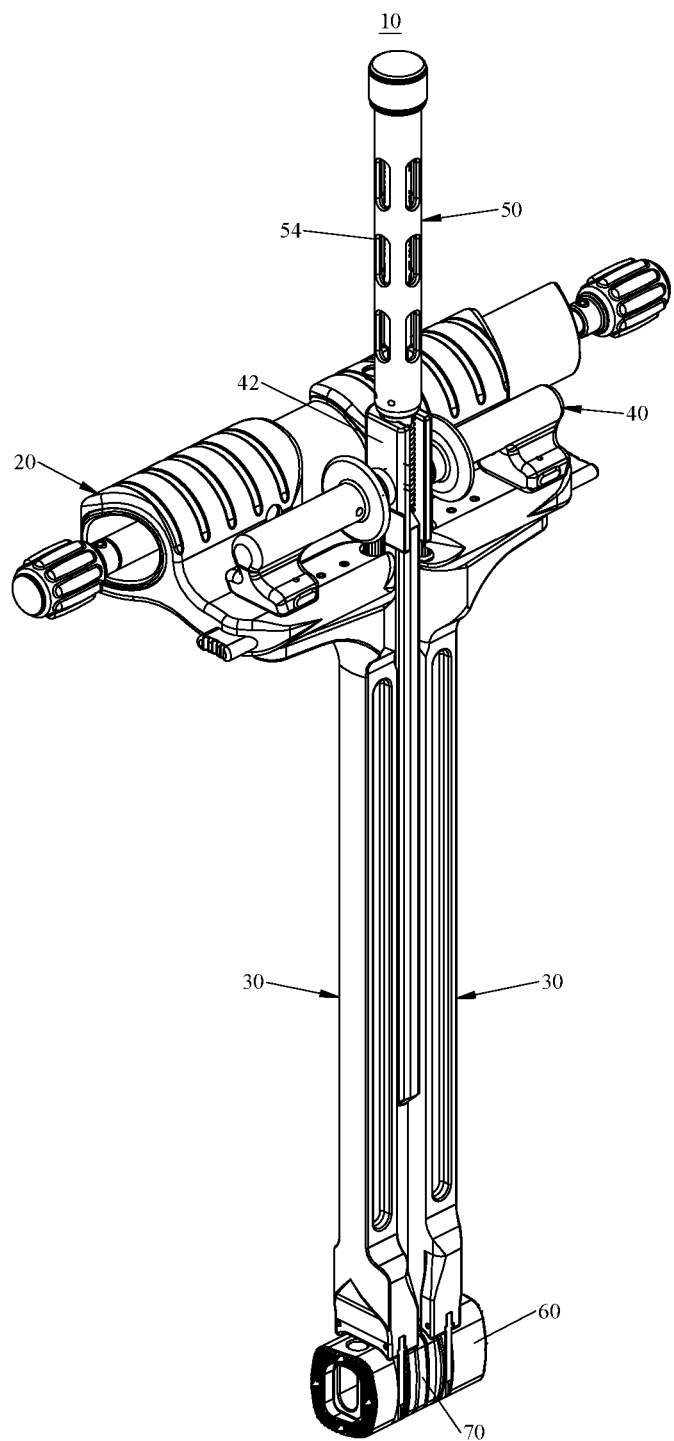
FIG. 1 is a perspective view of an embodiment of a distractor device in accordance with the present disclosure securing a clip to a cage.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. In addition, the term "cephalad" is used in this application to indicate a direction toward a patient's head, whereas the term "caudad" indicates a direction toward the patient's feet. Further still, for the purposes of this application, the term "lateral" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

Referring now to FIG. 1, an exemplary embodiment of a distractor device 10 provided in accordance with the present disclosure including a cage distractor 20, distractor blades 30, an inserter positioner 40, and a clip inserter 50. The device 10 is coupled to a cage 60.

Figure 2:
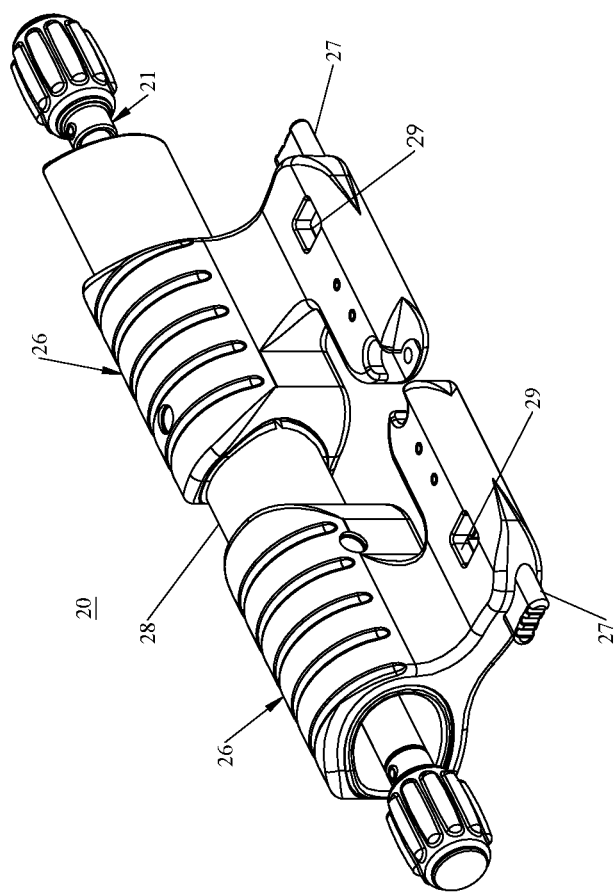
FIG. 2 is an enlarged perspective view of the cage distractor of the distractor device shown in FIG. 1.
Figure 3:
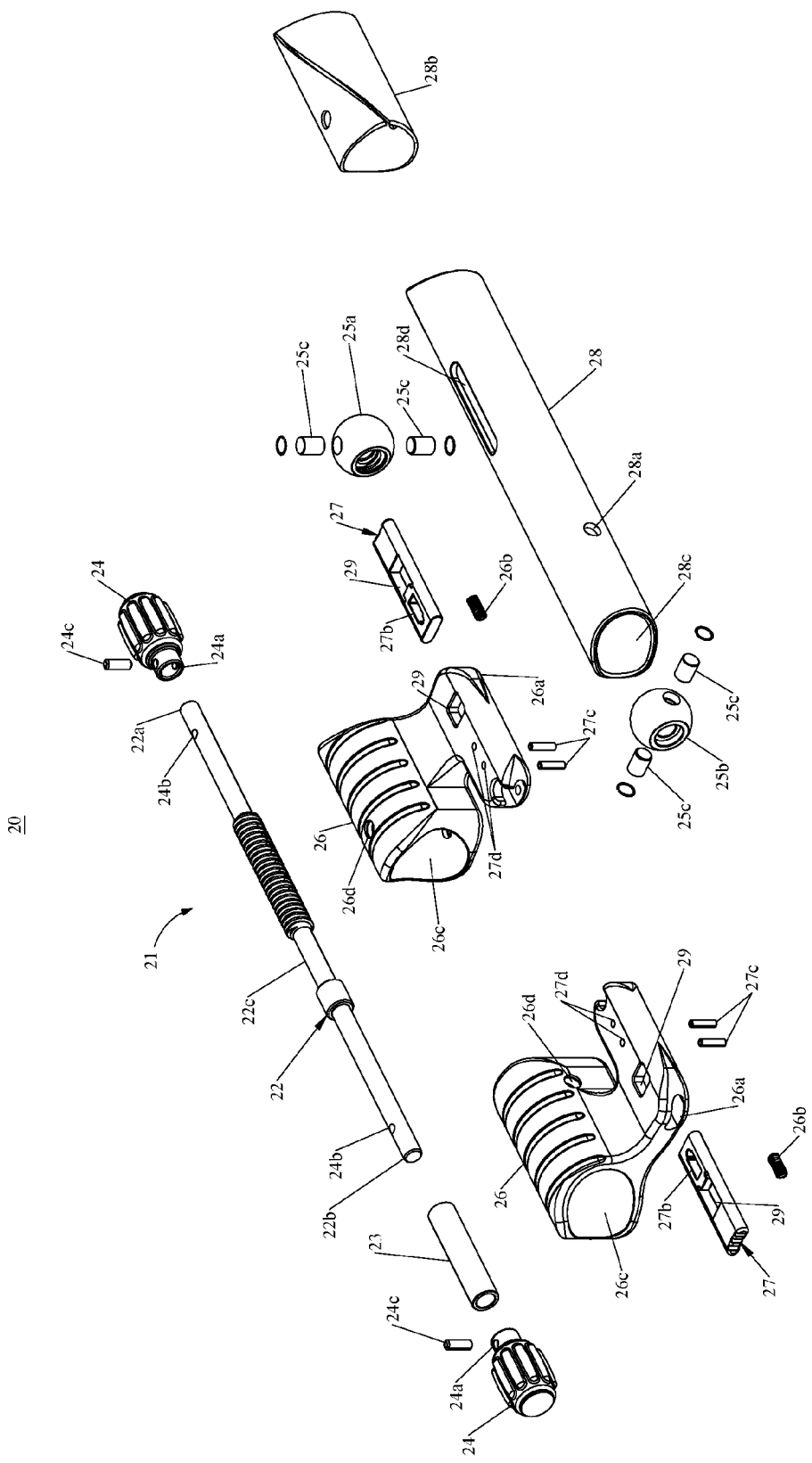
FIG. 3 is an exploded view, with parts separated, of the components of the cage distractor shown in FIG. 2.

With reference to FIGS. 2-3, the cage distractor 20 includes a center shaft assembly 21, distractor housings 26, and a support tube 28. The center shaft assembly 21 includes a center shaft 22, end bushing 23, knobs 24, and centering bushings 25a, 25b. The support tube 28 is disposed within a channel 26c defined through each of the distractor housings 26. The center shaft 22 is disposed in a shaft channel 28c defined through the support tube 28. The center shaft 22 is free to rotate within the shaft channel 28c. The center shaft 22 includes a first end portion 22a, a second end portion 22b, and a center portion 22c. One or both of the end portions 22a, 22b may have a diameter smaller than the diameter of the center portion 22c. A portion of the center portion 22c is threaded. The centering bushing 25a is positioned adjacent the first end portion 22a and includes a threaded section selectively engagable with the threaded portion of the center portion 22c. A pin 25c is inserted in a pinhole in the centering bushing 25a and inserted in a pinhole 26d in one of the distractor housings 26. The pin 25c that is inserted in the centering bushing 25a may be received through a pin slot 28d in the support tube 28. The centering bushing 25b is captured over the center shaft 22 between the center portion 22c and the end bushing 23. The centering bushing 25b is received within a bushing opening 26b in the other distractor housing 26b. Another pin 25c may be inserted in a pinhole in the centering bushing 25b and inserted into a pinhole 25d of the distractor housing 26 to secure the centering bushing in the distractor housing 26. As detailed below, as the threaded portion 22c threads through centering bushing 25a, the distractor housings 26 are moved, i.e., distracted or retracted, relative to one another. It will be appreciated that the centering bushings 25a, 25b are fixed to a respective distractor housing 26 such that as the threaded portion 22c threads thorough the centering bushing 25a, the centering bushings 25a, 25b move the distractor housings 26 relative to one another. The distractor housings 26 may move symmetrically to one another or move asymmetrically to one another. It will be appreciated that the centering shaft 22 is rotated within the channel 26c about an axis parallel to the movement, i.e., distraction or retraction, of the distractor housings 26. The support tube 28 is slidably received through each distractor housing 26 to provide rigidity to the distractor housings 26, i.e., to support the distractor housings 26 during the application of distraction force. The support tube 28 may include a second section 28b that is slidably received over the support tube 28 between the distractor housing 26 and the support tube 28. It is contemplated that the distractor housings 26 may also be manually moved, i.e., distracted or retracted, relative to one another by selectively disengaging one of the centering bushings 25a, 25b from the threaded portion of the center section 22c. It will be appreciated that centering bushing 25a allows for rotation about one axis and centering bushing 25b allows for rotation about another axis about the centering shaft 22. The configuration of the centering bushings 25a, 25b may reduce the possibility of binding caused by the loading and bending experienced during the distraction/retraction of the distractor housings 26, which may assist in permitting small adjustments in the relative positions of the distractor housings 26.

Each knob 24 is disposed over a respective end portion 22a, 22b of the center shaft 22. The knobs 24 are coupled to the center shaft 22 such that the center shaft 22 and the knobs 24 cooperate with the rotation of each other. The knobs 24 may be coupled to the center shaft 22 by pins 24c passing through openings 24b in the center shaft 22 and in pinholes 24a in the knobs 24. The end bushing 23 is disposed over the end portion 22b of the center shaft 22 between the center portion 22c and a respective knob 24. The end bushings 23 are free to rotate relative to the center shaft 22.

Figure 4:
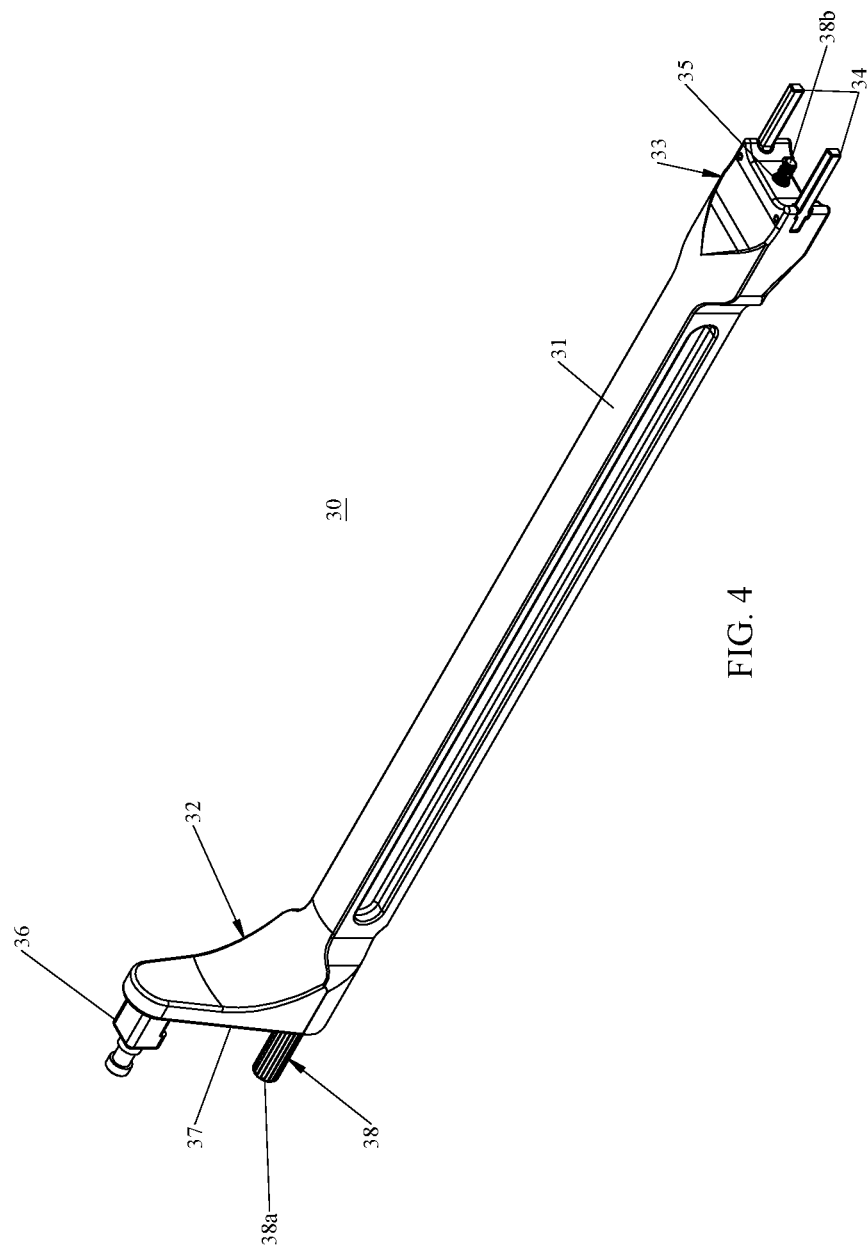
FIG. 4 is an enlarged perspective view of a distractor blade of the distractor device shown in FIG. 1.
Figure 5:
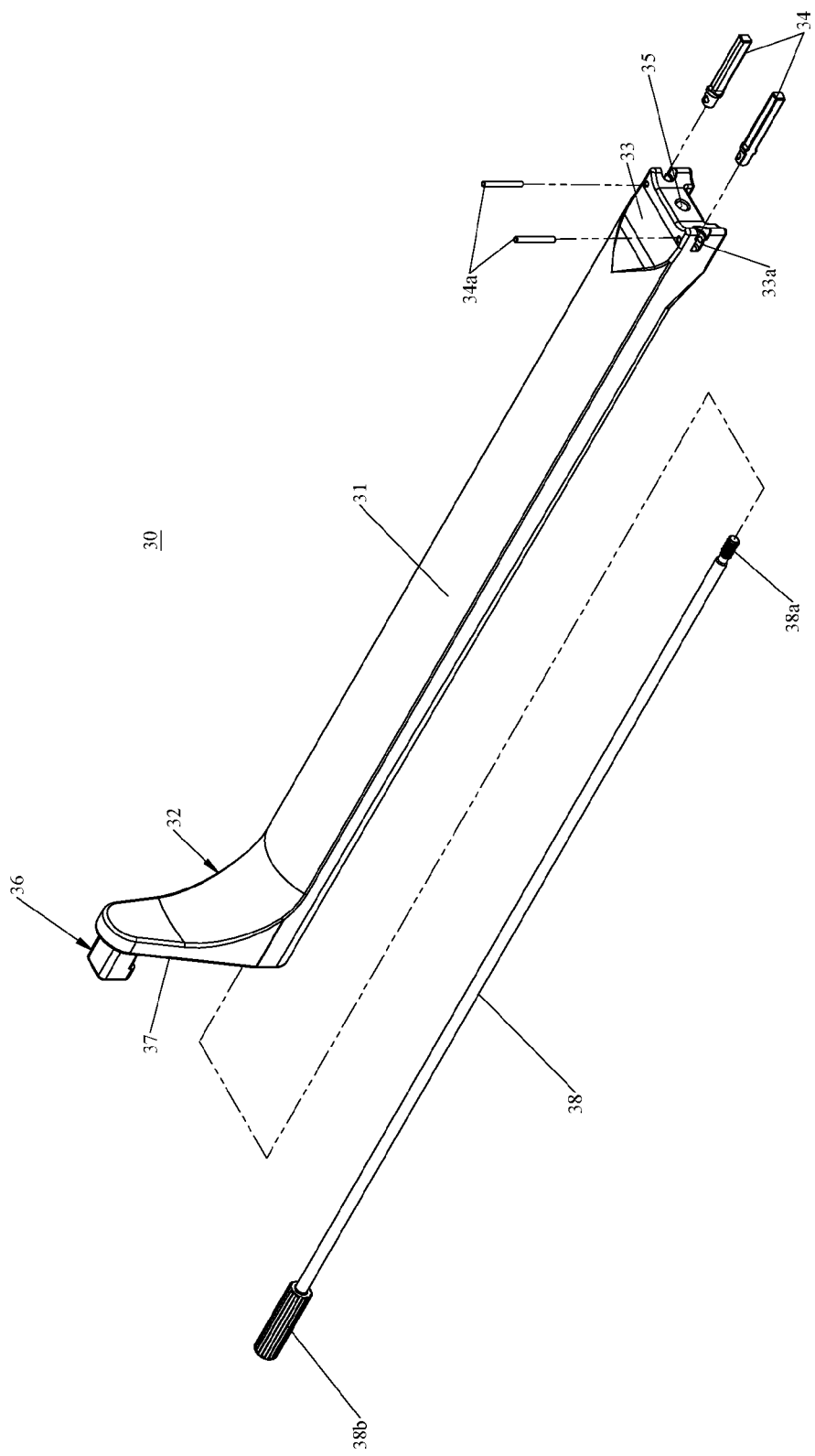
FIG. 5 is an exploded view, with parts separated, of the components of the distractor blade shown in FIG. 4.
Figure 6:
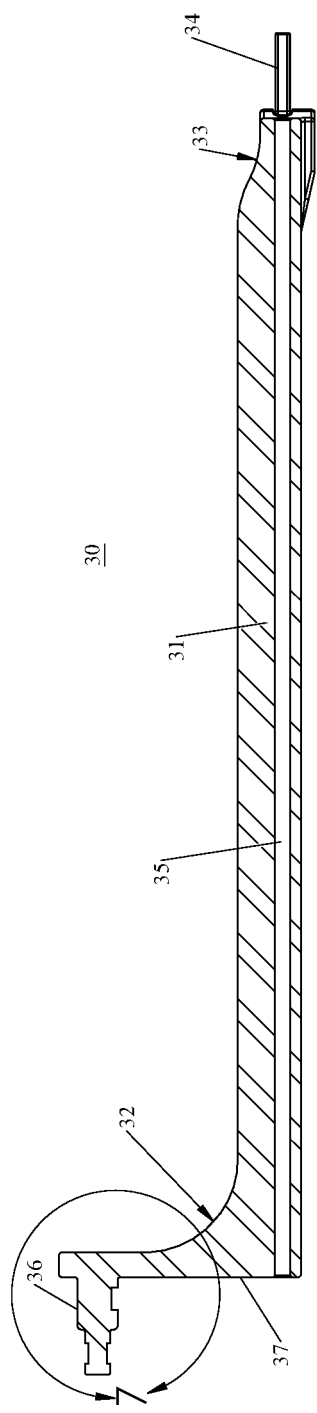
FIG. 6 is a side cross-sectional view taken along the center line of the elongated body of the distractor blade shown in FIG. 5.

With continued reference to FIGS. 2 and 3, each button 27 is slidably received within a button slot 26a in a respective distractor housing 26. Each button 27 and distractor housing 26 cooperate to form a protrusion passage 29 configured to capture a portion of a respective distractor blade 30 (FIG. 4) as detailed below. Each button 27 may be retained within the button slot 26a by a pin 27c slidably received through a pin slot 27b in the button and in pinholes 27d in the distractor housing 26. Each button 27 may be biased by a button biasing member 26b. Each button biasing member 26b may bias a respective button 27 outward or away from the other button 27.

Figure 7:
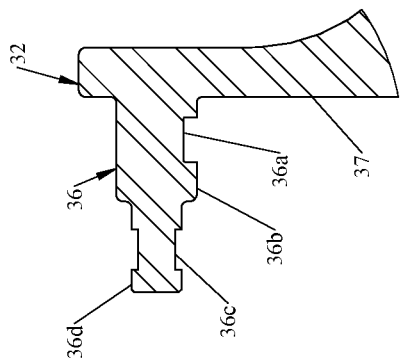
FIG. 7 is an enlargement of the detail area 7 shown in FIG. 6.

Referring now to FIGS. 4-7, each distractor blade 30 includes an elongated body 31, dovetail pins 34, and a blade shaft 38. The elongated body 31 includes a proximal end portion 32 and a distal end portion 33. The elongated body 31 defines a through passage 35 along a longitudinal axis of the elongated body 31. The proximal end portion 32 includes a protrusion 36 and a mating surface 37. The protrusion 36 extends from the mating surface 37 and includes, in order from the mating surface 37, a lower detent 36a, a lower lip 36b, an upper detent 36c, and an upper lip 36d, as best seen in FIG. 7. The lower lip 36b protrudes beyond the lower detent 36a. The lower lip 36b may have a dimension larger than a diameter of the upper lip 36d. The upper lip 36d extends beyond the upper detent 36c. The dovetail pins 34 are received within recesses 33a in the distal end portion 33 and extend from the distal end portion 33. The dovetail pins 34 may be retained in the recesses 33a by pins 34a sliding through openings in dovetail pins 34 and in pinholes of the distal end portion 33. The blade shaft 38 includes a grip 38b positioned at a proximal end and a threaded end 38a positioned at a distal end thereof. The blade shaft 38 is slidably received through the passage 35 of the elongated body 31 such that the threaded end 38a extends from the distal end portion 33 between the dovetail pins 34.

Figure 8:
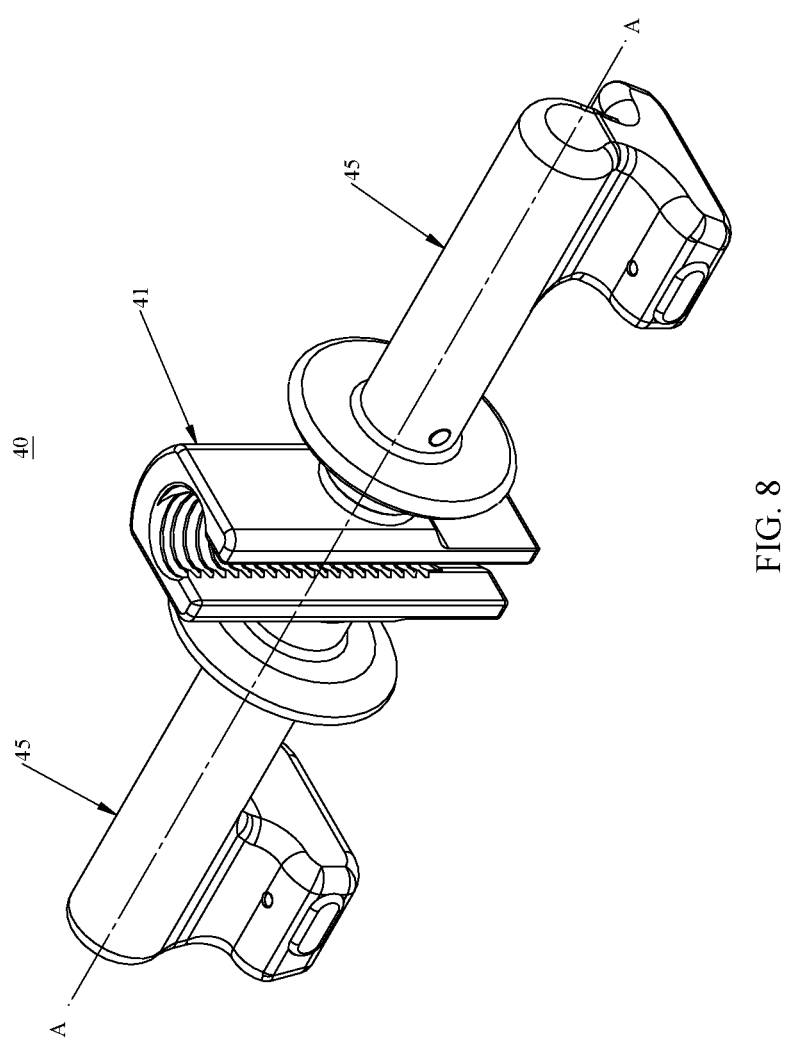
FIG. 8 is an enlarged perspective view of the inserter positioner of the distractor device shown in FIG. 1.
Figure 9:
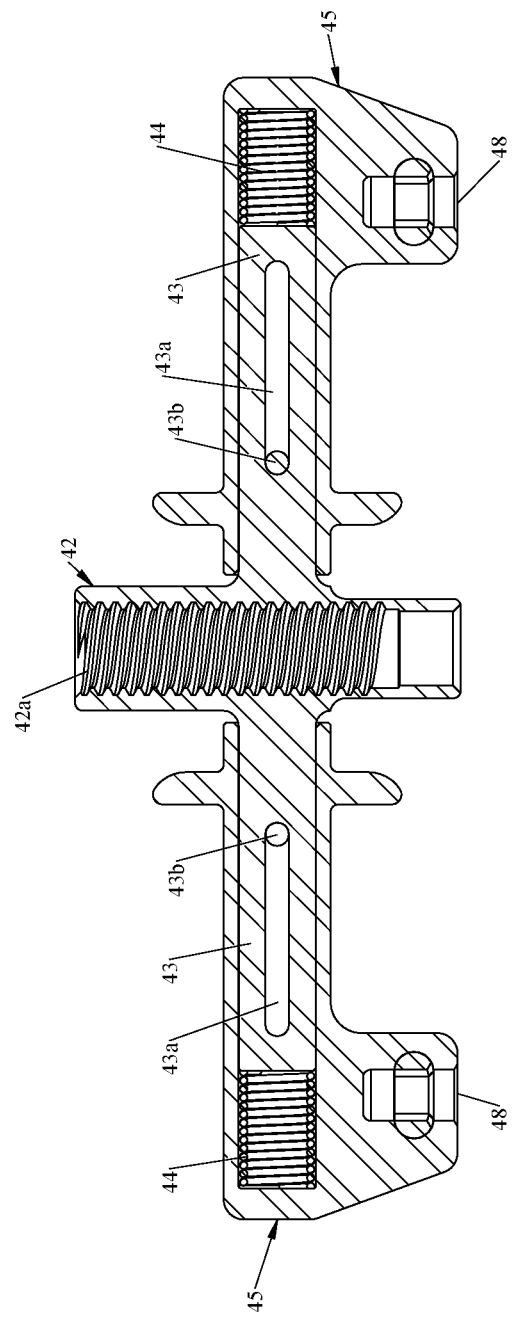
FIG. 9 is a front cross-sectional view of the inserter positioner of FIG. 8 taken along the axis A-A.
Figure 10:
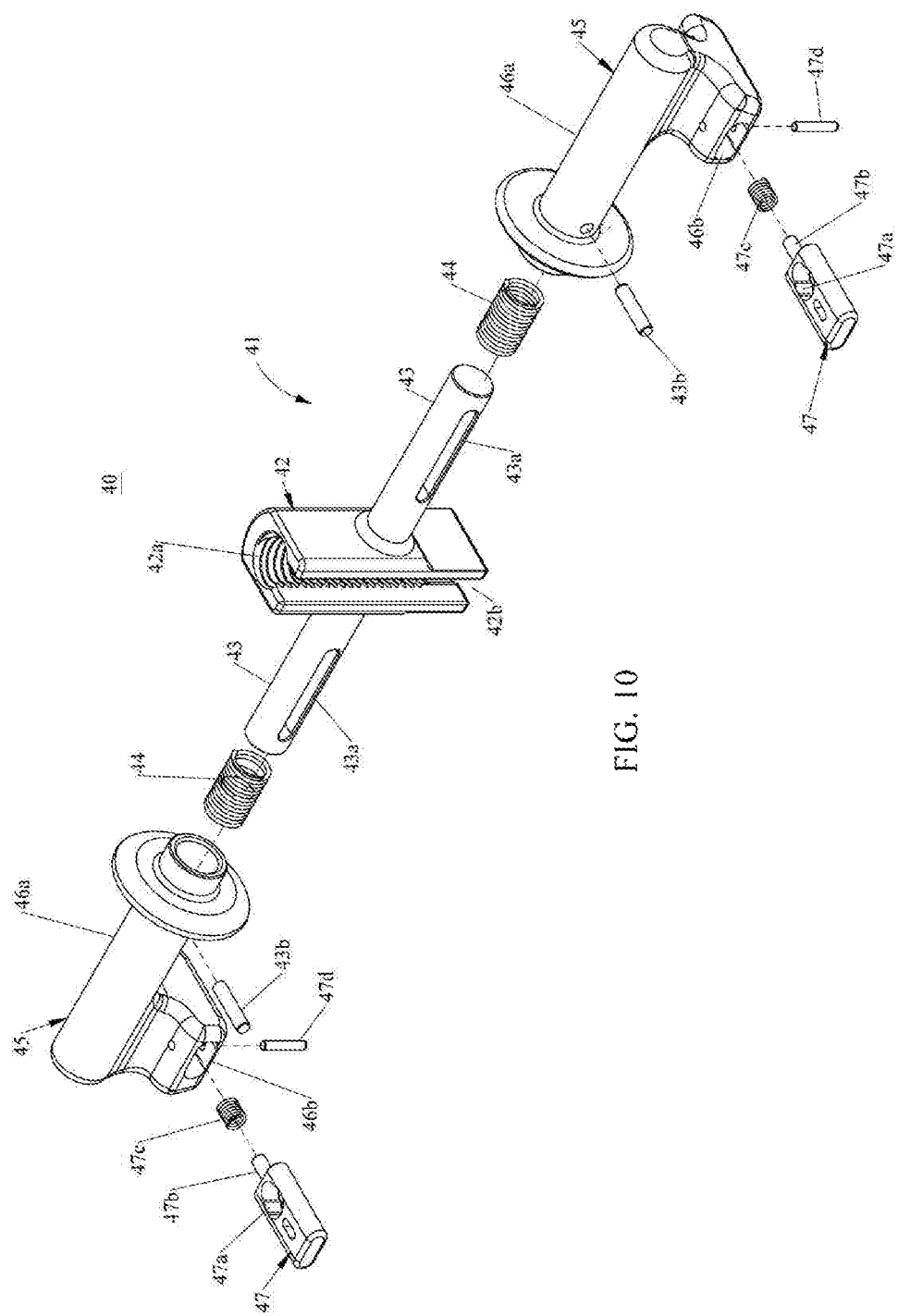
FIG. 10 is an exploded view, with parts separated, of the components of the inserter positioner shown in FIG. 8.

With reference to FIGS. 8-10, the inserter positioner 40 includes a center member 41, center member biasing members 44, and attachment members 45. The center member 41 defines an axis A-A and includes an inserter support 42 orthogonal to the axis A-A and centering rods 43. The inserter support 42 defines a threaded bore 42a and a keyway 42b. The keyway 42b extends through the front of the inserter support 42 (as viewed in FIG. 10) and into the threaded bore 42a. The centering rods 43 extend from the inserter support 42 in opposite directions along the axis A-A for substantially the same length. Each centering rod 43 includes a through pin slot 43a.

Each attachment member 45 includes a rod receiving portion 46a, a button receiving portion 46b, and a button 47. The rod receiving portion 46a is sized and configured to slide over a respective centering rod 43 of the center member 41. Each of the center member biasing members 44 is disposed within a respective rod receiving portion 46a between the end of the centering rod 43 and the end of the respective rod receiving portion 46a to center the inserter support 42 relative to the distractor blades 30 as detailed below. A sliding pin 43b is slidably received through the pin slot 43a in a respective centering rod 43 and in pinholes in a respective rod receiving portion 46a to retain the respective attachment member 45 to the center member 41.

Each button 47 defines a protrusion receiving hole 47a and includes a nub 47b. The protrusion receiving hole 47a passes through the top and bottom surfaces of the button 47. The button 47 is received within the button receiving portion 46b of a respective attachment member 45. The nub 47b extends from the button 47 towards the respective button receiving portion 46b. A button biasing member 47c is positioned over the nub 47b and is configured to bias the button 47 out of or away from the button receiving portion 46b. A pin 47d is slidably received in a pin slot defined in the button 47 and is in pinholes in the button receiving portion of the respective attachment member 45 to retain the button 47 within the button receiving portion 46b. The bottom of the button receiving portion 46b includes an blind hole 48 configured to receive the protrusion 36 of a respective blade 30 as detailed below.

Figure 11:
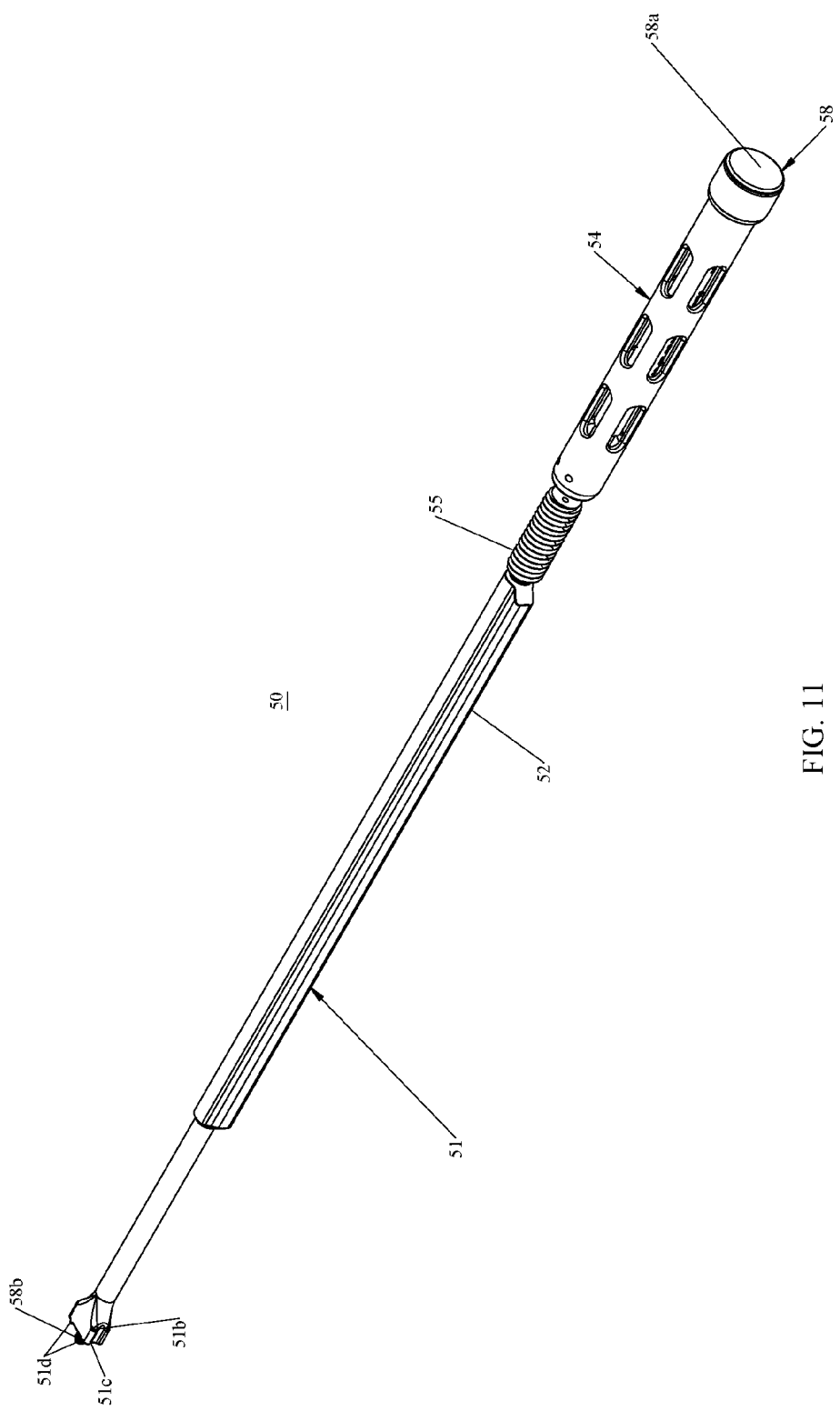
FIG. 11 is an enlarged perspective view of the clip inserter of the distractor device shown in FIG. 1.
Figure 12:
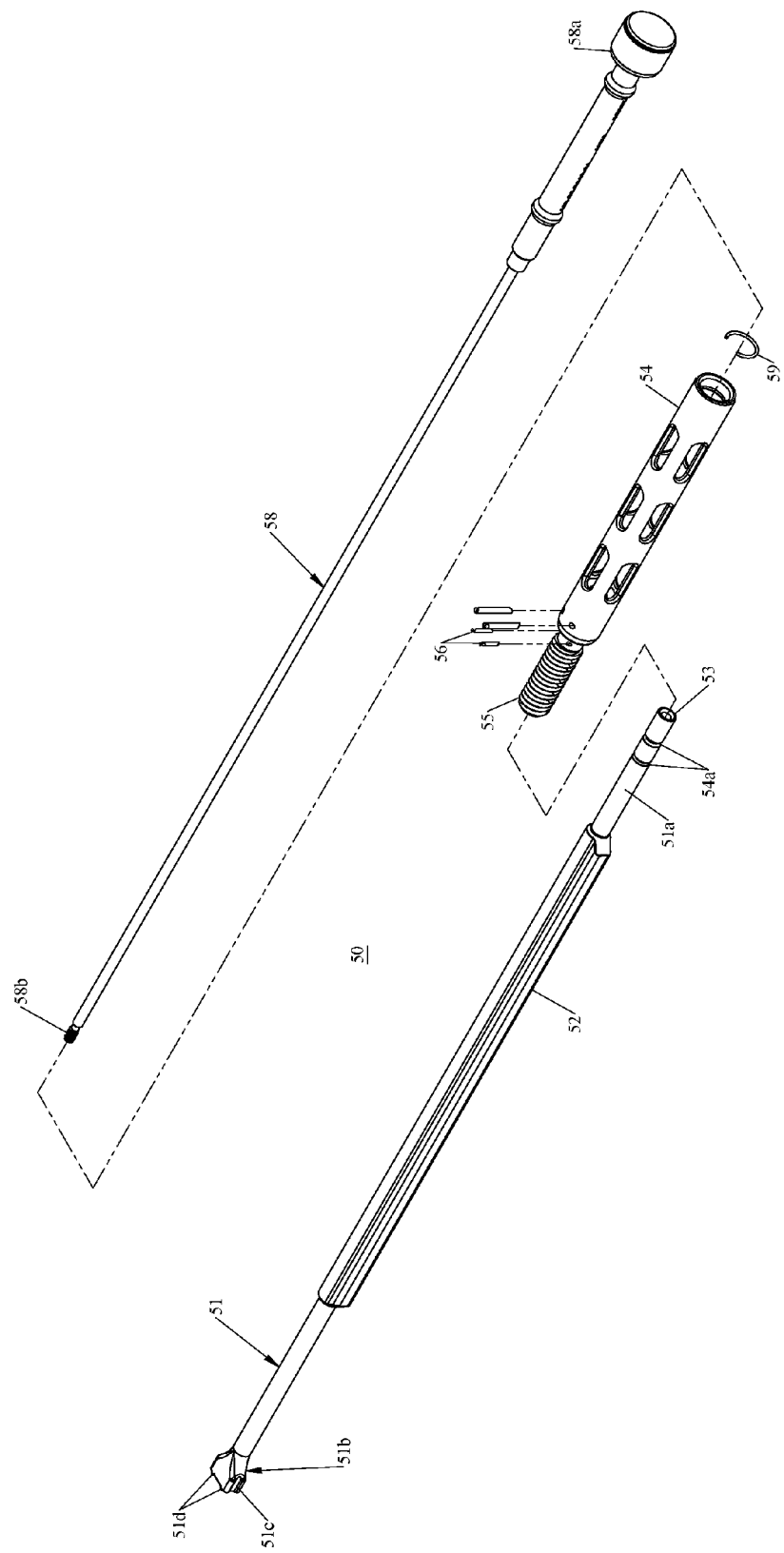
FIG. 12 is an exploded view, with parts separated, of the components of the clip inserter shown in FIG. 11.

Referring to FIGS. 11 and 12, the clip inserter 50 includes a cannulated body 51, a handle 54, and an inserter shaft 58. The cannulated body 51 defines a lumen 53 therethrough and includes a proximal end portion 51a, a distal end portion 51b, and a key 52. The distal end portion 51b includes recesses 51c and tips 51d configured to engage features of a clip 70 (FIG. 1) to secure and align the clip 70 with the distal end portion 51b. The key 52 is sized and configured to align the distal end portion 51b of the cannulated body 51 with the cage 60 (FIG. 1) as detailed below. The handle 54 includes a threaded handle end 55. The threaded handle end 55 is disposed over the proximal end portion 51a of the cannulated body 51. Handle pins 56 are inserted in pin holes in the handle 54 and are rotatably received by grooves 54a in the proximal end portion 51a such that the handle 55 is retained on and free to rotate about the proximal end portion 51a. The inserter shaft 58 has an inserter knob 58a positioned at a proximal end and a threaded end 58b positioned at a distal end thereof. The inserter shaft 58 is insertable through the handle 55 and the lumen 53 of the cannulated body 51 such that the threaded end 58b extends from the distal end 51b of the distal end portion 51b.

Figure 13:
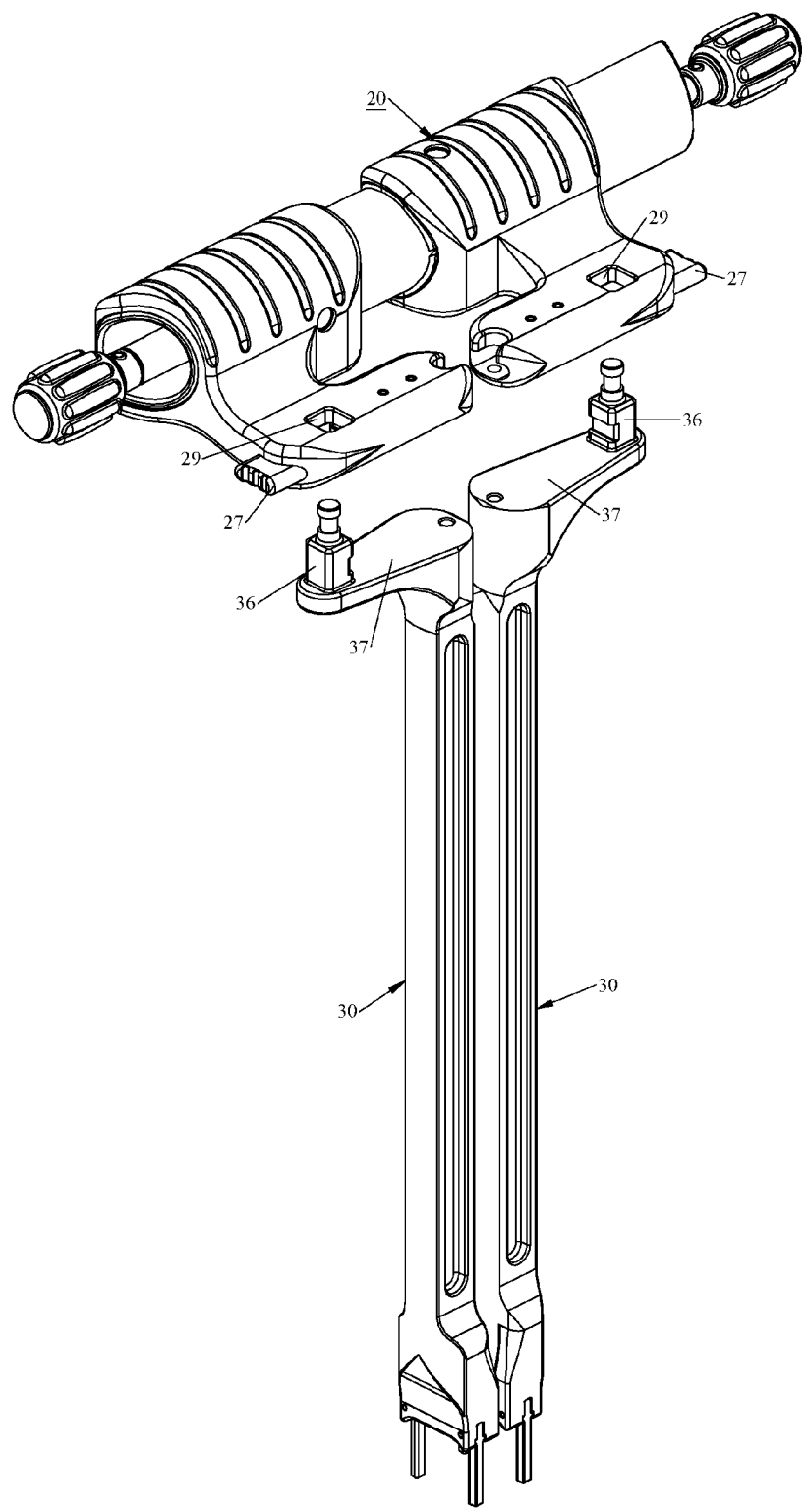
FIGS. 13-18 are a progression of perspective views showing the assembly of the distractor device shown in FIG. 1 on a cage to secure a clip to the cage in accordance with the present disclosure.
Figure 14:
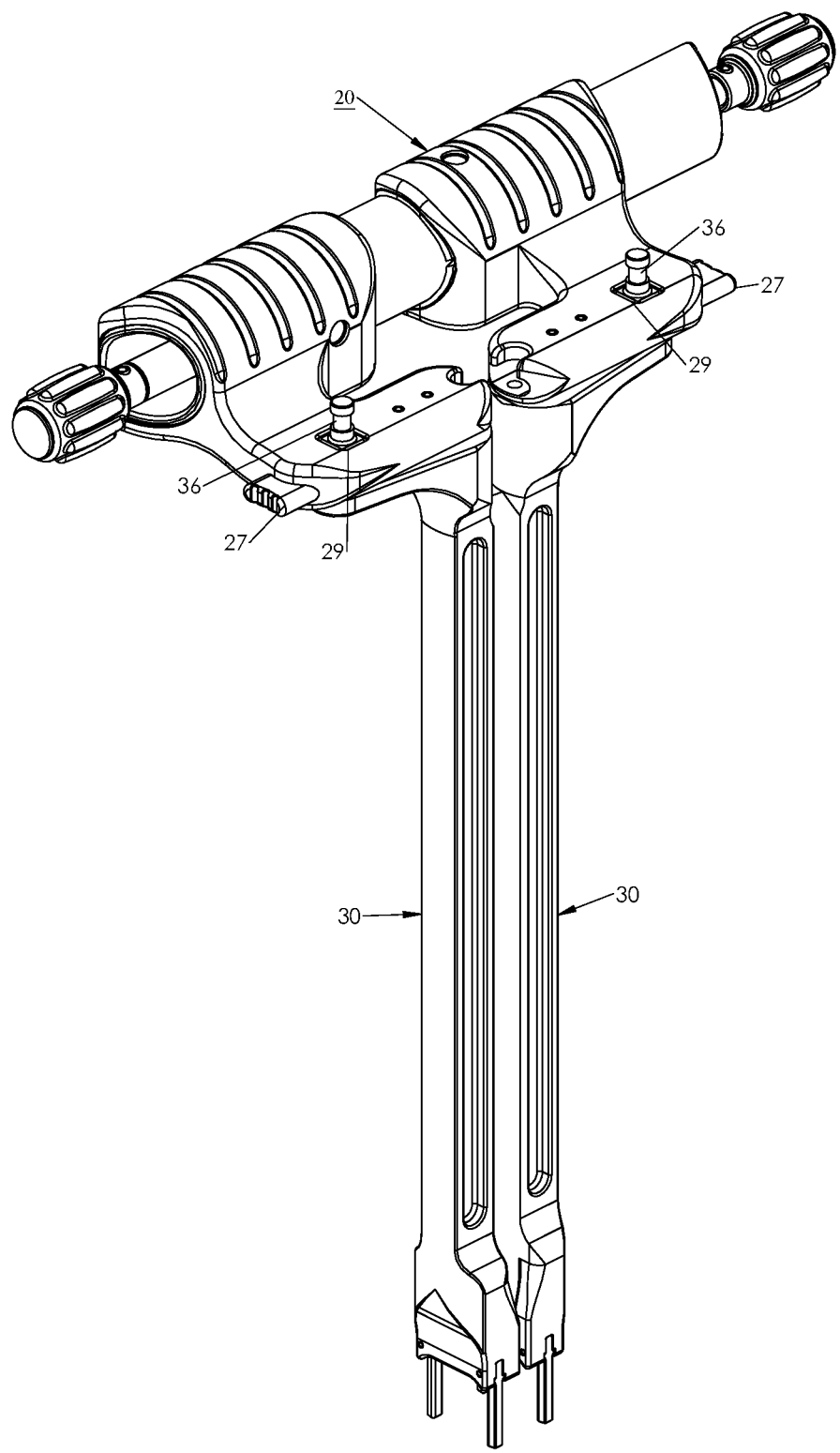

Referring to FIGS. 1 and 13-18, a method of assembling and using the distractor device 10 is detailed below in accordance with the present disclosure. The cage distractor 20 is positioned over the proximal end portion 32 of the distractor blades 30 as shown in FIG. 13. The protrusion 36 of each distractor blade 30 is inserted through a respective protrusion passage 29 of the cage distractor 20 until the matting surface 37 abuts the bottom surface of the cage distractor 20 as shown in FIG. 14. As each protrusion 36 passes through a respective protrusion passage 29, a respective button 27 is urged inward, against the button biasing member 26b (FIG. 3) as the lower lip 36b (FIG. 7) engages the respective button 27. Once the lower lip 36b passes through the respective button 27, the respective button 27 is urged outward by the button biasing member 26b such that the respective button 27 engages the lower detent 36a (FIG. 7) of the protrusion 36 to secure respective blade 30 to the cage distractor 20.

Figure 15:
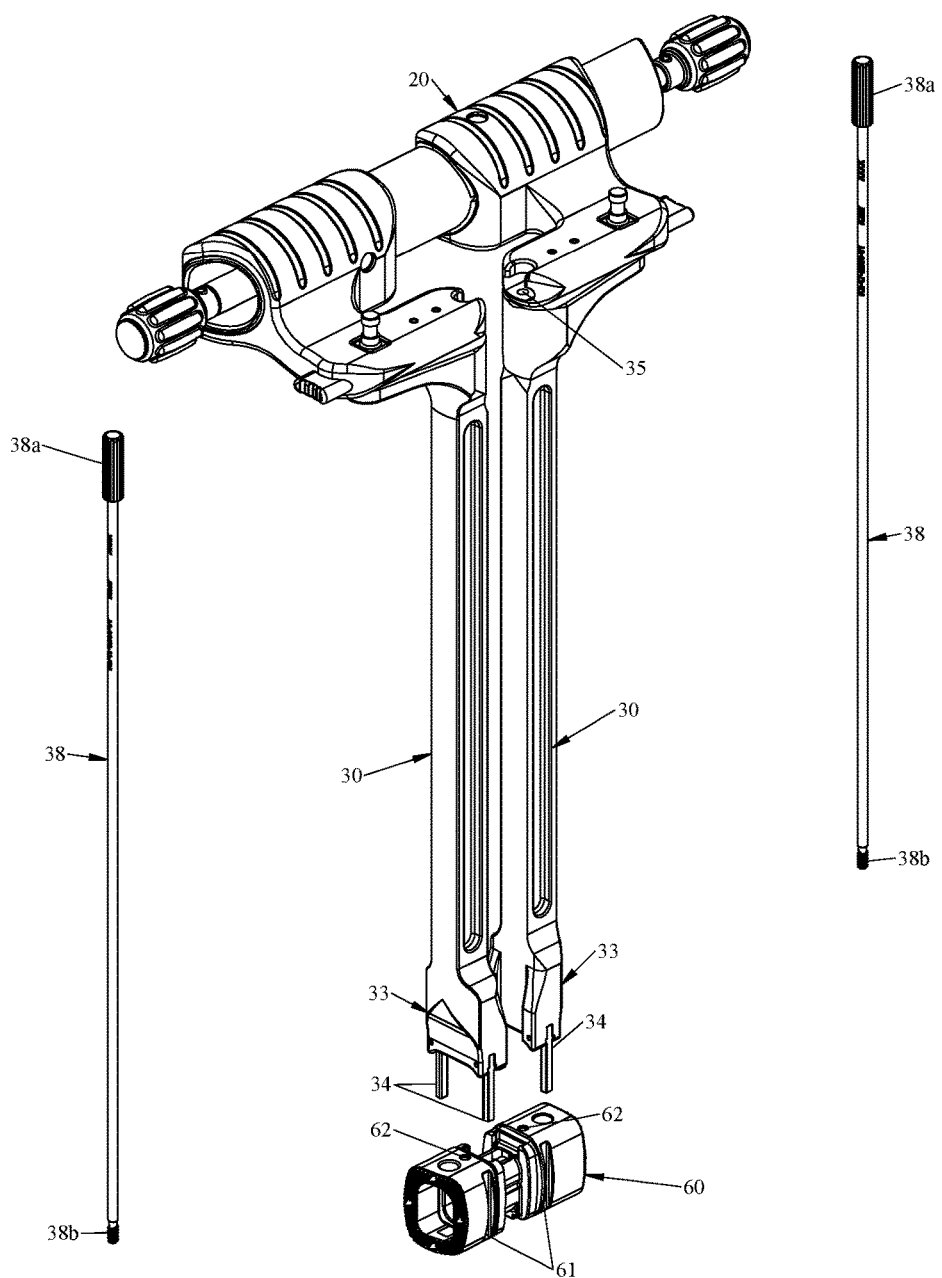
Figure 16:
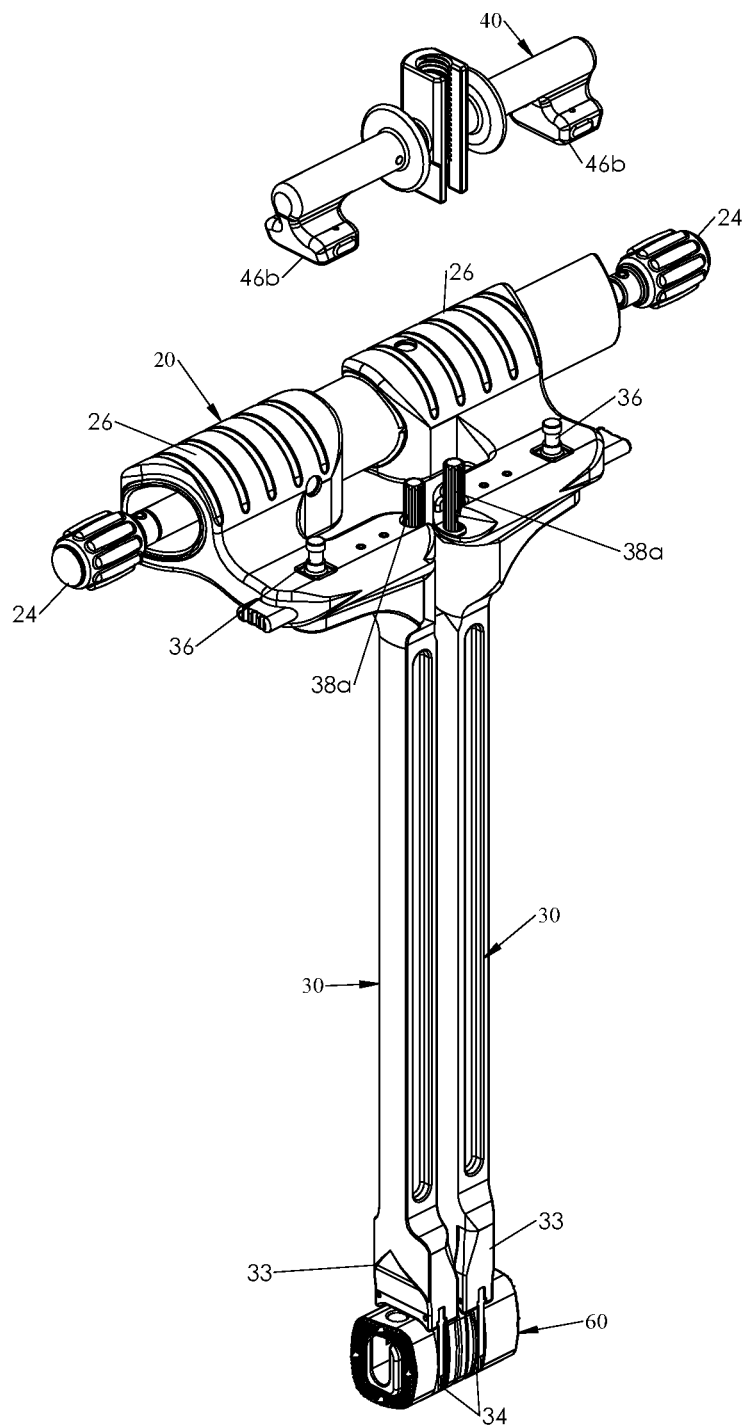

The cage distractor 20 with the blades 30 secured thereto is positioned over a cage 60 as shown in FIG. 15. The cage 60 is an expandable cage designed for supporting vertebrae and promoting spinal fusion. The cage is configured to be inserted in a space defined between two adjacent vertebrae. The height of the cage is adjustable between different heights by fixing first and second supporting members at different positions relative to one another. A clip 70 which engages a portion of the cage 60 between the first and second supporting members fixes the position of the first and second supporting members relative to one another. The clip 70 is configured to engage the cage 60 to secure the clip 70 to the cage 60. Such a cage and a clip are disclosed in co-owned U.S. patent application Ser. No. 12/602,898 filed Dec. 3, 2009, the content of which is incorporated in its entirety Each blade shaft 38 is inserted through the passage 35 (FIG. 6) of a respective blade 30 until the threaded end 38b engages a threaded hole 62 of the cage 60. The grip 38a of each blade shaft 38 is rotated to thread the threaded end 38b into the threaded hole 62 of the cage 60 until the cage 60 abuts and is secured to the distal end portion 33 of the respective blade 30. The dovetail pins 34 are slidably received by grooves 61 of the cage 60 to align the distal end portion 33 of the blades 30 with the cage 60 as shown in FIG. 16. In embodiments, each distraction blade 30 coupled to the cage 60 by the threading of the blade shafts 38. In some embodiments, each distraction blade 30 is coupled to the cage 60 by the friction fit of the dovetail pins 34 with the grooves 61. It is contemplated that the distraction blades 30 may be provided with only a blade shaft 38 to threadably couple to the cage 60 or only with dovetail pins 34 couple with the cage 60 by a friction fit or with both a blade shaft 38 and dovetail pins 34 to couple with the cage via threads and a friction fit.

The height of the cage 60 may be adjusted by moving the distractor housings 26 relative to one another. With continued reference to FIG. 16, the cage 60 is distracted by moving distractor housings 26 of the cage distractor 20 away from one another. The distractor housings 26 may be moved relative to one another by rotating the center shaft 22 to thread the threaded portion of the center portion 22c of the center shaft 22 through the centering bushings 25a, 25b (FIG. 3) to distract the distractor housings 26 away from one another. The knobs 24 may be rotated to rotate the center shaft 22. The knobs 24 may permit the distractor housings 26 to be moved incrementally. The knobs 24 may provide a mechanical advantage to increase the force used to move distractor housings 26 relative to one another. It is also contemplated that the distractor housings 26 may be moved towards one another in a similar manner as detailed above to retract the cage 60. It is also contemplated that the distractor housings 26 may be distracted by disengaging one of the centering bushings 25a, 25b from the threaded portion of the center portion 22c (FIG. 3) of the center shaft 22 and manually distracting the distractor housings 26 away from one another.

Figure 17:
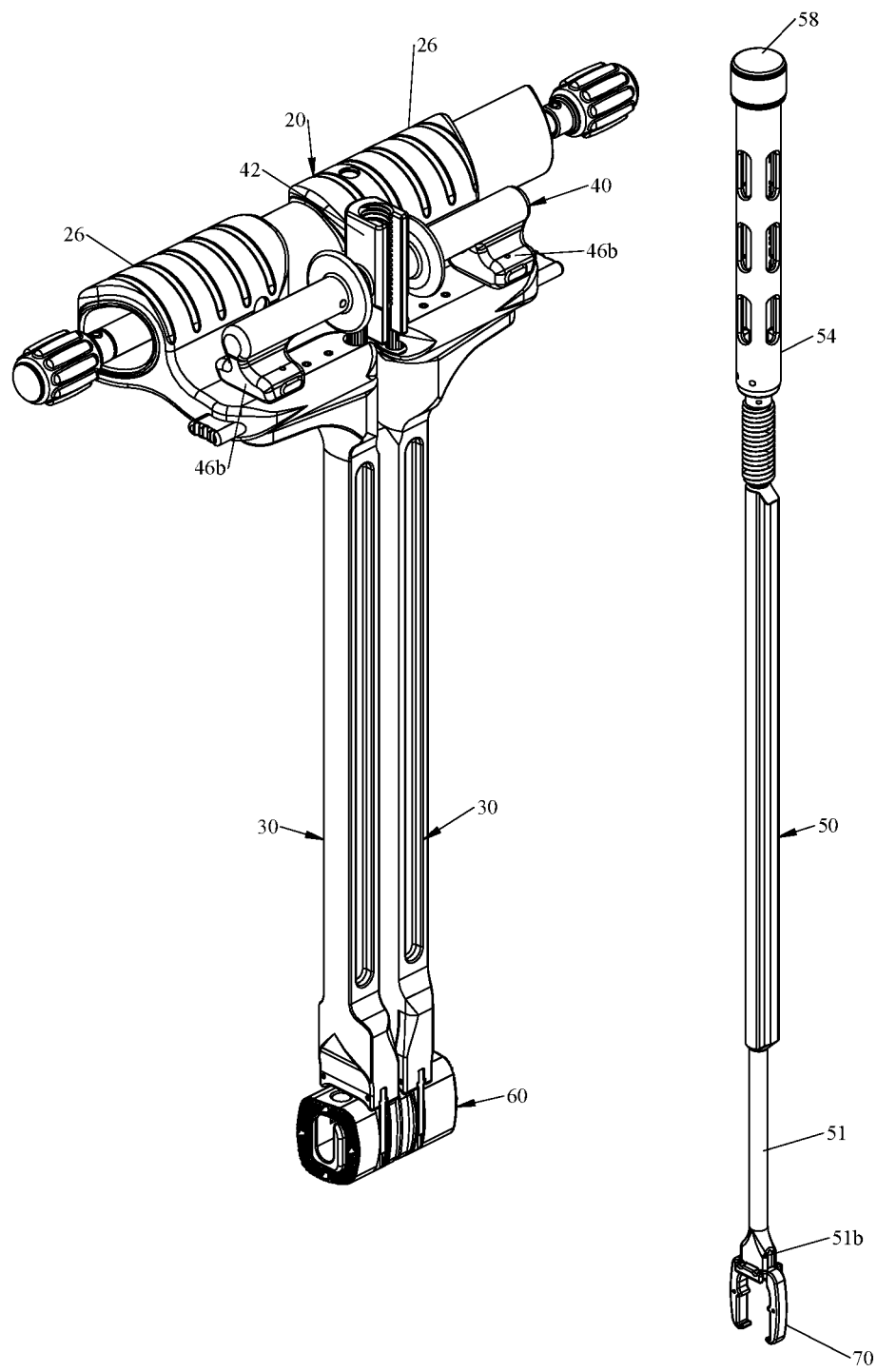

Continuing to refer to FIG. 16, the inserter positioner 40 is positioned over the cage distractor 20 and the protrusions 36 of the blades 30. The inserter positioner 40 is aligned such that the blind hole 48 (FIG. 9) of each button receiving portion 46b is adjacent a respective protrusion 36 of one of the blades 30. The blind holes 48 of the button receiving portions 46b are lowered onto the protrusions 36 such that the upper lip 36d (FIG. 7) of each protrusion 36 engages the protrusion receiving hole 47a (FIG. 10) of a respective button 47 to urge the respective button 47 against the button biasing member 47c (FIG. 10). As the lower surface of the inserter positioner 40 engages the upper surface of the distractor housings 26, the upper lip 36d passes through the protrusion receiving hole 47a and button 47 is urged by the button biasing member 47c to engage the upper detent 36c (FIG. 7) of the protrusion 36 such that the inserter positioner 40 is secured to the distractor housings 26 of the cage distractor 20 as shown in FIG. 17. When the inserter positioner 40 is secured to the distractor housings 26, the center member biasing members 44 (FIG. 10) center the inerter support 42 relative to the blades 30. The inserter positioner 40 may be attached to the distractor blades 30 before or after the distractor housings 26 are distracted.

With continued reference to FIG. 17, the clip 70 is secured to the distal end portion 51b of the clip inserter 50. The recesses 51c (FIG. 12) and the tips 51d (FIG. 12) of the distal end portion 51b engage features of the clip 70 to align the clip 70 with the clip inserter 50. The inserter shaft 58 is inserted through the handle 54 and the lumen 53 (FIG. 12) of the cannulated body 51 until the threaded end 58b (FIG. 12) engages a threaded hole (not shown) in the back of the clip 70 to secure the clip 70 to the clip inserter 50. The inserter knob 58a may be rotated to thread the threaded end 58b into the threaded hole in the back of the clip 70 to secure the clip 70 to the inserter clip inserter 50.

Figure 18:
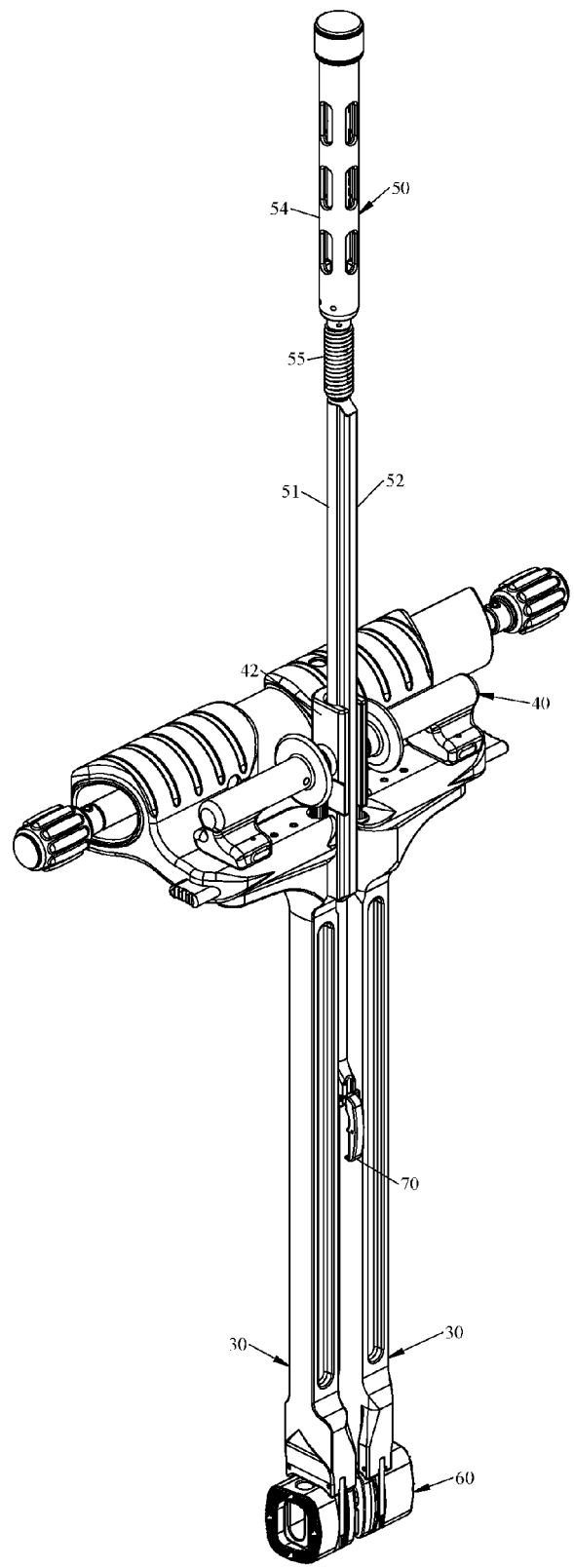

Referring to FIG. 18, the cannulated body 51 of the clip inserter 50 is slid through the threaded bore 42a (FIG. 10) of the inserter positioner 40 until the threaded handle end 55 abuts the threaded bore 42a. The key 52 is received by the keyway 42b (FIG. 10) to align the clip 70 with the cage 60. When the threaded handle end 55 abuts the threaded bore 42a, the clip 70 is adjacent to or engaged with the cage 60. The handle 54 is rotated to thread the threaded handle end 55 into threaded bore 42a to secure the clip 70 to the cage 60 as shown in FIG. 1. When the clip 70 is secured to the cage 60, e.g., by engagement features of the clip 70 engaging complimentary features on the cage 60, cage 60 is prevented from retracting by clip 70.

When the clip 70 is secured to the cage 60, the inserter shaft 58 is rotated to unthread the threaded end 58b from the threaded hole in the back of the clip 70. When the threaded end 58b is unthreaded from the clip 70, the handle 54 is rotated to remove the clip inserter 50 from the threaded bore 42*a* of the inserter positioner 40. The engagement features of the clip 70 and the cage 60 maintain the clip 70 on the cage 60.

The inserter positioner 40 is released from the distractor housings 26 and the blades 30 by pressing the buttons 47 inward, i.e., against the button biasing members 47*c*, to permit the upper lip 36*d* of each protrusion 36 to pass through the protrusion receiving hole 47*a* of each button 47. The blade shafts 38 are rotated to unthread the threaded ends 38*b* from the cage holes 62 and are removed from the passages 35 of the elongated bodies 31. When the blade shafts are unthreaded from the cage holes 62, the distractor device 10 may be removed from the cage 60. The blades 30 are disengaged from the distractor housings 26 of the cage distractor 20 by pressing buttons 27 inward to permit the lower lip 36*b* of each protrusion 36 to pass through the protrusion passage 29 of the distractor housings 26.

It is also contemplated that a first clip 70 may be replaced with a larger or smaller second clip 70 using the method described above. To remove the first clip 70, the clip inserter 50 is threaded into the clip positioner 40 before the second clip 70, to be inserted, is secured to the clip inserter 40. The inserter shaft 58 is threaded into the first clip 70, which is secured to the cage 60. The handle 54 is rotated to unthread the threaded handle end 55 from the threaded bore 42*a* of the center member 42. The unthreading of the threaded handle end 55 may provide a mechanical advantage to disengage the first clip 70 from the cage 60. When the first clip 70 is disengaged from the cage 60, the clip inserter 50 is removed from the clip positioner 40 as detailed above. The inserter shaft 58 is unthreaded from the first clip 70 to release the first clip 70 from the clip inserter 50. The second clip 70 is secured to the clip inserter 50 using the same inserter shaft 58 or a different inserter shaft 58 sized for the clip inserter 50. It is also contemplated, that a second clip inserter 50 may be used which is sized to the fit the second clip 70. When the second clip 70 is secured to the clip inserter, the second clip 70 is engaged to the cage 60 as detailed above.

According to aspects of the present disclosure, a distraction kit includes a distraction device and an assortment of clips. The distraction device included in the distraction kit may be any embodiment of the distraction device 10 detailed above. Each of the clips in the assortment of clips may be substantially similar to clip 70 detailed above and may have a different width corresponding to a different height of distraction of a cage. The kit may include an assortment of clip inserters substantially similar to clip inserter 50, detailed above, with each clip inserter engagable with one or more of the assortment of clips. The kit may include a plurality of pairs of first and second distraction blades 30. Each of the plurality of pairs of first and second distraction blades defining a different length between the proximal and distal end portions thereof.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A method of distracting a cage, the method comprising:
securing a proximal end portion of a first distractor blade in a first distractor housing of a cage distractor and securing a proximal end portion of a second distractor blade in a second distractor housing of the cage distractor;
sliding a distal end portion of the first distractor blade and a distal end portion of the second distractor blade onto a cage;
rotating a center shaft of the cage distractor to move the first distractor housing away from the second distractor housing such that the distal end portion of the first distractor blade moves away from the distal end portion of the second distractor blade to distract the cage, wherein the center shaft is disposed along an axis parallel to the movement of the first distractor housing away from the second distractor housing; and
securing at least one of the first and second distractor blades to the cage with a blade shaft inserted through a passage of the at least one of the first and second distractor blades and threading a threaded end of the blade shaft into a threaded hole in the cage.

2. A method of distracting a cage, the method comprising:
securing a proximal end portion of a first distractor blade in a first distractor housing of a cage distractor and securing a proximal end portion of a second distractor blade in a second distractor housing of the cage distractor;
sliding a distal end portion of the first distractor blade and a distal end portion of the second distractor blade onto a cage;
rotating a center shaft of the cage distractor to move the first distractor housing away from the second distractor housing such that the distal end portion of the first distractor blade moves away from the distal end portion of the second distractor blade to distract the cage, wherein the center shaft is disposed along an axis parallel to the movement of the first distractor housing away from the second distractor housing;
securing a clip positioner to the proximal end portion of the first distractor blade and the proximal end portion of the second distractor blade, the clip positioner including a center member centered between the first and second distractor blades;
securing a clip to a distal end portion of a clip inserter; and
sliding the clip inserter through a bore of the center member to center the clip between the distal end portions of the first and second distractor blades.

3. The method according to claim 2, wherein securing the clip to the distal end portion of the clip inserter includes threading a threaded end of an inserter shaft passed through a cannula of a cannulated body of the clip inserter into a threaded hole in the clip.

4. The method according to claim 2, wherein the bore of the center member is a threaded bore and the clip inserter includes a handle having a threaded handle end, the handle rotatable about a cannulated body portion of the clip inserter, and wherein securing the clip onto the cage includes threading the threaded handle end into the threaded bore.

* * * * *